Figure 1:
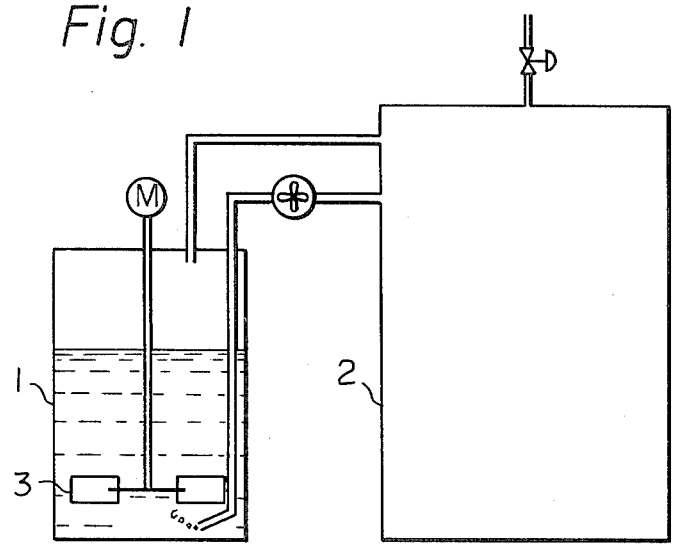

United States Patent [19]

Ishikawa et al.

[11] 4,225,381

[45] Sep. 30, 1980

[54] METHOD FOR REMOVING ODOR FROM FLUID

[75] Inventors: Hisao Ishikawa; Yukio Kita; Kouki Horikoshi, all of Tokyo, Japan

[73] Assignee: Oji Paper Co., Ltd., Tokyo, Japan

[21] Appl. No.: 968,637

[22] Filed: Dec. 12, 1978

[51] Int. Cl.² .............................................. D21C 11/08
[52] U.S. Cl. ......................................... 162/51; 55/73; 210/611; 435/262; 422/4; 422/5; 423/242; 423/243
[58] Field of Search ............... 162/29, 51; 195/2, 3 H, 195/81; 210/2, 11; 55/99, 279, 73; 422/4, 5; 423/242, 243, 242 R; 435/262, 281, 282, 925, 913, 945, 933, 931

[56] References Cited

FOREIGN PATENT DOCUMENTS

| 2558256 | 7/1977 | Fed. Rep. of Germany | 55/73 |
| 50-26761 | 3/1975 | Japan | 210/11 |
| 51-63554 | 6/1976 | Japan | 210/11 |

*Primary Examiner*—William F. Smith
*Attorney, Agent, or Firm*—Armstrong, Nikaido, Marmelstein & Kubovcik

[57] ABSTRACT

A method for removing malodorous sulfur compounds from a fluid containing such compounds. In this method, fungi belonging to genera Cephalosporium, Paecilomyces, Penicillium, Aspergillus, Trichoderma and Mucor can be used for effectively removing malodorous sulfur compounds from a fluid.

2 Claims, 3 Drawing Figures

METHOD FOR REMOVING ODOR FROM FLUID

The present invention relates to a method for removing odor from fluids such as liquid, gas or a mixture thereof, and more particularly, it relates to a method for biological deodorization of fluids containing malodorous substances derived from sulfur compounds.

Bad odor substances derived from sulfur compounds (or malodorous sulfur compounds) such as hydrogen sulfide, methyl mercaptan, dimethyl sulfide, dimethyl disulfide, thiophene and the like are generated in, for instance, pulp and paper industry mills, petroleum industry plants, sewage treatment plants and plants for treating fish wastes, such as fish bones and entrails. Such malodorous sulfur compounds have been heretofore discharged into waste waters and the open air. However, these malodorous sulfur compounds cause serious unpleasant odor problems for residents in the local area. Recently, in order to prevent such air pollution, various processes for removing bad odors from fluid effluents have been developed and have been used in unpleasant odor generating sources.

Processes for removing odors from fluids can be typically divided into two groups, that is, physicochemical processes and biological processes. The process for removing odors from fluids according to the present invention belongs to the latter group. In the conventional biological processes for deodorizing or decomposing malodorous sulfur compounds, there are only known those in which sulfur bacteria are used (see Japanese Patent Laid-Open Applications Nos. 50-69278/75 and 51-63554/76) and in which bacteria, genus Pseudomonas are used (see "Petroleum Fermentation", edited by Petroleum Fermentation Society, p490, published on Sept. 1, 1970, Saiwai Shobo, Tokyo, Japan).

The object of the present invention is to provide a novel method for biologically removing odors from fluids containing malodorous sulfur compounds.

Other objects and advantages of the present invention will become clear from the following description.

In accordance with the present invention, there is provided a method for removing odors from fluids containing malodorous substances derived from sulfur compounds comprising the step of contacting the fluid with fungi.

The inventors have diligently studied micro-organisms which are capable of removing malodorous sulfur compounds from fluid containing the same. As a result of their studies, the inventors have found that numerous strains of fungi which are isolated from the natural environment by using a conventional technique can effectively remove malodorous sulfur compounds from fluid containing the same.

Typical examples of the fungi used in the present invention are Cephalosporium, such as Cephalosporium sp. FERM-P No. 3976 (which has been deposited in the Fermentation Research Institute, Inage, Chiba-ken, Japan; all the numbers hereinafter recited refer to the numbers of this Institute) and Cephalosporium sp. FERM-P No. 3977; Paecilomyces, such as Penicillium sp. FERM-P No. 3978 (although this micro-organism has been deposited as Penicillium, it is clarified as Paecilomyces by the identification after the deposition); Penicillium, such as Penicillium sp. FERM-P No. 3979; Aspergillus, such as Aspergillus sp. FERM-P No. 3980; Mucor, such as Mucor sp. FERM-P No. 3981, and; Trichoderma, such as Trichoderma sp. FERM-P No. 3982. Morphological characteristics of these fungi, and aspects of growth and colors of the fungi on various plate cultures are shown in Table 1 below. The growth temperature of the plate cultures was 30° C.

TABLE 1-1

| Strain | Cephalosporium sp. FERM-P No. 3976 | Cephalosporium sp. FERM-P No. 3977 |
|---|---|---|
| Morphological characteristics | Hyphae septate, Conidiophores arise as side branches of aerial hyphae, errect, tapering, 20-70 × 2-3 μ. Conidia elliptical, 5-11 × 2-3 μ. | Hyphae sparsely septate. Aerial hyphae floccose, predominantly funiculose with conidiophores arising as short side branches, 15-27 × 2-4 μ. Conidia elliptical, 6-9 × 2-3 μ. |
| Aspect of growth characteristics on plate agar | Colonies spreading, moderate-growing, umbonate, floccose aerial phypae, at first white, later becoming brownish white. | Colonies spreading, moderate-growing, convex, at first white, later becoming pinkish white. |
| Malt extract agar | (G) moderate<br>(CO) white → brownish white<br>(CR) white or pale reddish yellow → pale reddish yellow or light brown<br>(SP) dull yellow red | (G) moderate or scanty<br>(CO) white → pinkish white<br>(CR) pinkish white - purplish red<br>(SP) none |
| Potato dextrose agar | (G) moderate<br>(CO) white → brownish white<br>(CR) white or yellowish white - pale yellow red<br>(SP) dull yellow red | (G) moderate<br>(CO) white → pinkish white<br>(CR) white → dark brown purple<br>(SP) dark brown purple |
| Czapek's agar | (G) moderate or scanty<br>(CO) white → brownish white<br>(CR) white or light brownish gray → pale yellow brown or dark brown<br>(SP) dull yellow red | (G) moderate or scanty<br>(CO) white<br>(CR) white → pale yellow red or bluish black<br>(SP) dull red |
| Sabouraud agar | (G) moderate<br>(CO) white → pinkish white or brownish white<br>(CR) white → purplish red<br>(SP) pale purplish red | (G) moderate<br>(CO) white → pinkish white<br>(CR) pinkish white → pale yellow red or dull red<br>(SP) pale yellow brown |

TABLE 1-1-continued

| Strain | Cephalosporium sp. FERM-P No. 3976 | Cephalosporium sp. FERM-P No. 3977 |
|---|---|---|
| Oatmeal agar | (G) moderate<br>(CO) white → brownish white<br>(CR) white → pale yellow red<br>(SP) dull yellow red | (G) moderate or scanty<br>(CO) white → pinkish white<br>(CR) white → grayish red purple<br>(SP) grayish red purple |
| Synthetic agar for mucor | (G) moderate<br>(CO) white<br>(CR) white → pale yellow or reddish yellow<br>(SP) pale yellow | (G) moderate<br>(CO) white → yellowish white<br>(CR) white → yellow gray or light reddish yellow<br>(SP) pale yellow |
| YpSs agar | (G) moderate<br>(CO) white → brownish white<br>(CR) pale reddish yellow → pale brown or brown purple | (G) moderate<br>(CO) white<br>(CR) yellowish white → pale yellow red or dark red purple<br>(SP) dull red |
| Yeast sucrose agar | (G) moderate<br>(CO) white → brownish white<br>(CR) pale reddish yellow → dull yellow red or brown purple<br>(SR) dull yellow red | (G) moderate<br>(CO) white → purplish white<br>(CR) pale yellow red → dark brown purpose<br>(SP) light purplish gray |

(Atten.)
(G) Growth
(CO) Color of colony
(CR) Color of colony reverse
(SP) Soluble pigment into substratum

TABLE 1-2

| Strain | Penicillium sp. FERM-P No. 3978 | Pencillium sp. FERM-P No. 3979 |
|---|---|---|
| Morphological characteristics | Conidiophores arise from aerial hyphae, generally short. The conidial fructification is in two stages, the branches of the conidiophore bearing a terminal verticil of divergent metulae, with divergent phialides. Conidial chains long, elliptical, smooth, 2.5 × 5 μ. | Aerial hyphae hyalin, septate, Conidiophores somewhat roughened, penicilli asymmetrica. Conidia elliptical to subglobose, 2 × 2.5 μ. |
| Aspect of growth characteristics on plate agar | Colonies spreading, convex floccose aerial hyphae, becoming powdery when mature, at first white later becoming light olive. | Colonies slowly spreading, very closely floccose almost velvety, white at first, becoming pinkish gray. |
| Malt extract agar | (G) abundant<br>(CO) yellowish white → light olive<br>(CR) yellowish white → dark olive<br>(SP) none | (G) moderate<br>(CO) white → pinkish gray<br>(CR) yellowish white - pale yellow or pale pink<br>(SP) none |
| Potato dextrose agar | (G) abundant<br>(CO) yellowish white → light olive<br>(CR) yellowish white → dark yellow brown<br>(SP) none | (G) moderate<br>(CO) white → pinkish gray<br>(CR) white → pinkish white or pale yellow red<br>(SP) none |
| Czapak's agar | (G) moderate<br>(CO) white → light olive<br>(CR) white → dark yellow brown or yellow<br>(SP) light brownish gray | (G) moderate<br>(CO) white → pale red purple<br>(CR) white → grayish red purple<br>(SP) grayish red purple |
| Sabouraud agar | (G) abundant<br>(CO) yellowish white → light olive<br>(CR) yellowish white → dark yellow brown<br>(SP) grayish yellow green | (G) moderate<br>(CO) white → pale red purple<br>(CR) yellowish white → yellow brown<br>(SP) pale yellow |
| Oatmeal agar | (G) moderate<br>(CO) white → light olive<br>(CR) white → olive green or yellowish white<br>(SP) light brownish gray | (G) moderate<br>(CO) white → pale pink<br>(CR) white → pale pink<br>(SP) none |
| Synthetic agar for Mucor | (G) abundant<br>(CO) white → light olive<br>(CR) white → dark yellow brown<br>(SP) none | (G) moderate<br>(CO) white → pinkish gray<br>(CR) white → pale pink<br>(SP) none |
| YpSs agar | (G) abundant<br>(CO) white → light olive<br>(CR) yellowish white → yellow | (G) moderate<br>(CO) white → dark reddish gray<br>(CR) white → pale yellow red |

TABLE 1-2-continued

| Strain | Penicillium sp. FERM-P No. 3978 | Pencillium sp. FERM-P No. 3979 |
|---|---|---|
| Yeast sucrose agar | or yellow brown<br>(SP) grayish yellow green<br>(G) abundant<br>(CO) white → light olive<br>(CR) yellowish white → yellow brown<br>(SP) light brownish gray | or light reddish purple<br>(SP) none<br>(G) moderate<br>(CO) white → pinkish gray<br>(CR) white → pale pink or pinkish gray<br>(SP) none |

(Atten.)
(G) Growth
(CO) Color of colony
(CR) Color of colony reverse
(SP) Soluble pigment into substratum

TABLE 1-3

| Strain | Aspergillus sp. FERM-P No. 3980 | Mucor sp. FERM-P No. 3981 |
|---|---|---|
| Morphological characteristics | Conidial heads mostly globose, others somewhat loosely radiate. Conidiophores arise mostly from aerial hyphae, roughened. Vesicles almost globose, 10–15 $\mu$ in diameter. Phialides 7–8 × 2.5 $\mu$, in a single series. Conidia almost globose, smooth, mostly 3–4 $\mu$. | Turf short, up to 4 mm, in height. Sporangiophores usually sympodially branched. Sporangia usually 30–50 $\mu$ in diameter. Columellae elliptical, 20 $\mu$ long, spores elliptical 3 × 5 $\mu$. Chlamydospores present, 20–40 $\mu$ in diameter. |
| Aspect of growth characteristics on plate agar | Colonies spreading, generally abundant growing, convex, at first white, later becoming olive. | Colonies spreading, generally abundant growing, convex, yellowish gray. Sporulation on Czapek's and oatmeal agar scanty. |
| Malt extract agar | (G) abundant<br>(CO) white or yellow green → dark greenish yellow<br>(CR) pale yellow → pale yellow brown<br>(SR) none | (G) abundant<br>(CO) pale yellow brown → yellowish gray<br>(CR) pale yellow or yellow → pale yellow red<br>(SP) none |
| Potato dextrose agar | (G) abundant<br>(CO) white or yellow green → dark greenish yellow<br>(CR) yellowish white → pale olive<br>(SP) pale yellow red | (G) abundant<br>(CO) pale yellow → yellowish gray<br>(CR) pale yellow → pale yellow red<br>(SP) none |
| Czapek's agar | (G) abundant<br>(CO) white → light olive<br>(CR) yellowish white → pale reddish yellow or yellow brown<br>(SP) pale reddish yellow | (G) moderate or scanty<br>(CO) white → pale yellow<br>(CR) white → pale yellow<br>(SP) none |
| Sabouraud agar | (G) moderate<br>(CO) white → dark greenish yellow<br>(CR) white → pale yellow green<br>(SP) pale yellow red | (G) abundant<br>(CO) pale yellow → yellowish gray<br>(CR) pale yellow or yellow → reddish yellow or yellow brown<br>(SP) none |
| Oatmeal agar | (G) moderate<br>(CO) white - dark greenish yellow<br>(CR) white - pale yellow green<br>(SP) pale yellow red | (G) moderate<br>(CO) white → yellowish white<br>(CR) white<br>(SP) none |
| Synthetic agar for Mucor | (G) abundant<br>(CO) white or yellow green → dark yellow green<br>(CR) yellowish white → pale yellow green<br>(SP) none | (G) abundant<br>(CO) pale yellow → yellowish gray<br>(CR) yellowish white or yellow → reddish yellow<br>(SP) none |
| YpSs agar | (G) abundant<br>(CO) white or yellow green → dark yellow green<br>(CR) yellowish white → pale yellow green or light reddish yellow<br>(SP) none | (G) abundant<br>(CO) pale yellow → yellowish gray<br>(CR) pale yellow → yellowish gray or pale yellow red<br>(SP) none |
| Yeast sucrose agar | (G) abundant<br>(CO) white or dark yellow green → olive<br>(CR) pale yellow brown → light | (G) abundant<br>(CO) pale yellow → yellowish gray<br>(CR) pale yellow → pale reddish |

TABLE 1-3-continued

| Strain | Aspergillus sp. FERM-P No. 3980 | Mucor sp. FERM-P No. 3981 |
|---|---|---|
| | olive (SP) pale yellow red | yellow or brown (SP) none |

(Atten.)
(G) Growth
(CO) Color of colony
(CR) Color of colony reverse
(SP) Soluble pigment into substratum

TABLE 1-4

| Strain | Trichoderma sp. FERM-P No. 3982 |
|---|---|
| Morphological characteristics | Hyphae septate. Conidiophores arise as short branches of aerial hyphae, branching usually opposite, not swollen at the apex, up to 60 μ in height. Conidia almost globose, smooth 3-4 μ. |
| Aspect of growth characteristics on plate agar | Colonies spreading, generally abundant growing, flat, at first white, later becoming dark bluish green. |
| Malt extract agar | (G) abundant (CO) white → dark bluish green (CR) yellow → pale yellow red (SP) reddish yellow |
| Potato dextrose agar | (G) abundant (CO) white → dark bluish green (CR) pale yellow → brown (SP) yellow red |
| Czapek's agar | (G) moderate or scanty (CO) white → dark bluish green (CR) white → pale green (SP) none |
| Sabouraud agar | (G) abundant (CO) white → pale yellow brown (CR) pale yellow red → yellowish brown (SP) pale yellow |
| Oatmeal agar | (G) abundant or moderate (CO) white → dark bluish green (CR) white → yellow brown (SP) pale yellow |
| Synthetic agar for Mucor | (G) abundant (CO) white → white or dark yellow green (CR) white or pale yellow → light reddish yellow (SP) light reddish yellow |
| YpSs agar | (G) abundant (CO) white → dark bluish green (CR) white → pale yellow (SP) yellowish gray |
| Yeast sucrose agar | (G) abundant (CO) white → dark bluish green (CR) yellow → pale yellow brown (SP) dark yellow |

(Atten.)
(G) Growth
(CO) Color of colony
(CR) Color of colony reverse
(SP) Soluble pigment into substratum Based on the following literature and the results listed in Table 1, it was confirmed that each isolated strain belongs to the stated genus. The literatures are: Mycologia 58, p351-361(1966), R. S. Sukapure et al; K. B. Raper and C. Thom "A Manual of the Penicillia" (1949); C. Thom and K. B. Raper "A Manual of the Aspergilli" (1945); H. Zycha "Kryptogamenflora der Mark Brandenburg Pilze II Mucorineae" (1935), and; J. C. Gilman "A Manual of Soil Fungi" (1957). Both of the above-mentioned Cephalosporium sp. FERM-P No. 3976 and FERM-P No. 3977 belong to genus Cephalosporium. However, Cephalosporium sp. FERM-P No. 3976 is clearly different from Cephalosporium sp. FERM-P No. 3977, because the conidiophores of the former are longer than those of the latter and, also, because the aerial hyphae of the former become funiculose.

Figure 2:
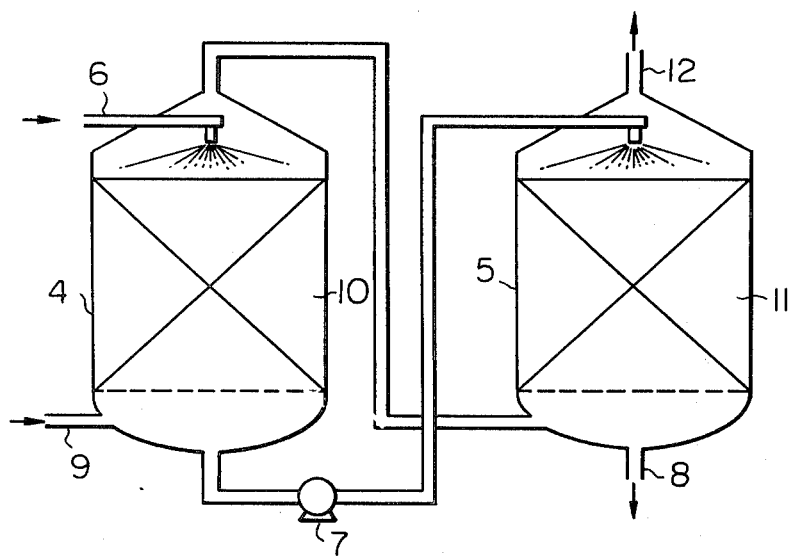
Figure 3:
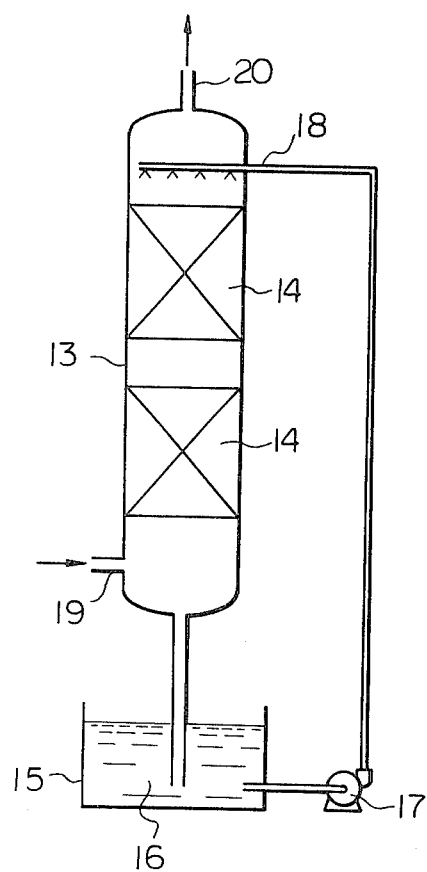

The present invention will be better understood from the description set forth below with reference to the accompanying drawings, but is by no means limited to those drawings. In the drawings:

FIGS. 1 through 3 are schematic drawings illustrating the typical embodiments of the method of the present invention in which fluids containing malodorous sulfur compounds are biologically deodorized by using fungi.

The fungi mentioned hereinabove can be used alone or in any combination thereof. A fungus which is capable of remarkably decomposing certain malodorous sulfur compound or compounds can be conveniently used in combination with another fungus which is capable of remarkably decomposing another malodorous sulfur compound or compounds.

As shown in FIG. 1, a fluid containing malodorous sulfur compounds is batchwise treated in a cultivation vessel 1 provided with an agitator 3. Charged into the vessel 1 are cells of the above-mentioned fungus, and nutrients, such as glucose, waste molasses, methanol; $NH_4NO_3$, $(NH_4)_2SO_4$, $KNO_3$, urea, pepton; corn steep liquor and the like, and a fluid to be deodorized is added into the system. When the fluid is a liquid, it is added into the vessel 1, and the fluid and the fungus are placed in contact with each other under agitation, while oxygen (or air) contained in a gas holder 2 is blown into the liquid in the vessel 1, by means of a suitable blower. The gas in the vapor zone in the vessel is returned to the gas holder and recirculated into the liquid in the vessel 1. Thus, the malodorous sulfur compounds contained in both liquid and vapor zone are decomposed. When a fluid is a gas, it is charged into the gas holder 2 together with oxygen (or air). The gas contained in the gas holder 2 is blown into the liquid in the vessel 1 which contains the fungus and the necessary nutrients. Thus, the malodorous sulfur compounds contained in the gas to be treated are decomposed by contact with the fungus.

As shown in FIG. 2, a fluid containing malodorous sulfur compounds can be also treated in, for example, trickling filters. A liquid containing malodorous sulfur compounds is fed to the top of a first trickling filter 4 through a liquid feed pipe 6, whereas oxygen or air is blown into the bottom of the first trickling filter 4 through a gas feed pipe 9. The first trickling filter 4 comprises a filtering medium 10, such as blast furnace slags, wood chips, plastic packings and the like. The filtering medium 10 is pre-treated with a culture medium containing a strain of the above-mentioned fungus and the necessary nutrients, whereby the culture medium is previously fixed to the filtering medium. Thus, the malodorous sulfur compounds contained in the liquid are decomposed by the fungus under an aeration condition. The treated liquid is then fed, via a pump 7, to a second trickling filter 5 provided with a filtering medium 11, which is also pre-treated with a culture medium containing the fungus and the necessary nutrients. The second trickling filter 5 is similar to the first trickling filter 4. The liquid is purified in the second tricling filter 5 in the same way as in the first tricling filter 4. The treated liquid is discharged from a liquid discharge pipe 8 and returned to the liquid feed pipe 6 by means of, for example, a suitable pump. The liquid can be stored in a storage vessel (not shown in FIG. 2), if it is preferable. On the other hand, a gas effluent from the top of the first trickling filter 4 enters into the bottom of the second trickling filter 5, where the gas, which is slightly contaminated with the malodorous sulfur compounds, is also biologically treated. The treated gas is discharged into the outside atmosphere, through a gas discharge pipe 12.

If a gas containing malodorous sulfur compounds is deodorized, the gas can be fed through the pipe 9, whereby the gas is brought into countercurrent contact with a circulating liquid in the filtering medium. Thus, a malodorous gas can be deodorized.

As shown in FIG. 3, a fluid containing malodorous sulfur compounds can be further treated in, for example, a packed column 13 packed with suitable plastic packings 14, such as those used in the conventional absorbers and distillation columns. According to this embodiment, a gas containing malodorous sulfur compounds together with oxygen (or air) is fed through a gas inlet 19, whereas a circulating liquid 16 contained in a vessel 15 is circulated via a pump 17 to the top 18 of the column 13. The liquid contains the above-mentioned fungus and the necessary nutrients. Thus, the gas is brought into countercurrent contact with the circulating liquid in the packed column 13, whereby the malodorous sulfur compounds are decomposed by the action of the fungus. The treated deodorized gas is discharged from the outlet 20 of the column 13.

As mentioned above, the method for removing odor from a fluid according to the present invention can be carried out in the above-mentioned various ways.

Although the operating conditions can be chosen within wide ranges, the temperature of the liquid (or culture modium) is preferably within the range of from about 25° C. to about 35° C., and the pH of the liquid (or culture medium) is preferably within the range of from about 3 to about 6. The content of the fungus in the liquid phase of the vessel 1 may be varied within a wide range, but will preferably be in the range of from about 0.05 to about 0.5% by weight, and more preferably in the range of from about 0.1 to about 0.3% by weight.

The present invention will be further illustrated by, but is by no means limited to, the following examples. The concentrations of the malodorous sulfur compounds were determined according to FPD gas chromatography. When the fluid to be treated was liquid, head gas was sampled under gas-liquid equilibrium state, and when the fluid to be treated was gas, feed and discharge gases were sampled.

EXAMPLE 1

Into 1 liter of an evaporator condensate discharged from a kraft pulp mill, 1 g of $NH_4NO_3$, 1 g of $KH_2PO_4$, 0.5 g of $MgCl_2.6H_2O$ and 0.5 g of yeast extract were added and the mixture was then sterilized. 50 ml of the pre-culture of each fungus listed in Table 2, which were incubated in the same culture medium for 3 days, was inoculated into the mixture and then cultured in a 2 liter closed cultivation vessel 1, provided with an agitator 3 (see FIG. 1), at a temperature of 30° C., for 3 days. The cultivation vessel 1 was connected to a 5 liter gas holder 2 filled with pure oxygen gas. The oxygen was bubbled into the mixture contained in the vessel 1. The results are shown in Table 2 below.

TABLE 2

| Fungi | Gas Concentration in Gas Phase after 3 days' cultivation (ppm) | | | |
|---|---|---|---|---|
| | $H_2S$ | $CH_3SH$ | $(CH_3)_2S$ | $(CH_3)_2S_2$ |
| Control* | 1.5 | 52 | 85 | 90 |
| Cephalosporium sp. FERM-P No. 3977 | 0.1 | 0.1 | 0.5 | 2.8 |
| Penicillium sp. FERM-P No. 3978 | 0.1 | 0.5 | 5.0 | 10 |
| Penicillium sp. FERM-P No. 3979 | 0.1 | 0.5 | 7.9 | 15 |
| Mucor sp. FERM-P No. 3981 | 0.1 | 0.1 | 0.5 | 17 |
| Trichoderma sp. FERM-P No. 3982 | 0.1 | 0.5 | 7.0 | 16 |

*No fungi were inoculated.

As is clear from Table 2, the malodorous sulfur compounds were remarkably removed from the condensate by the use of each fungus. When $MgSO_4.7H_2O$ was used instead of $MgCl_2.6H_2O$, similar results were obtained.

EXAMPLE 2

An evaporator condensate discharged from a kraft pulp mill was treated by using an apparatus as illustrated in FIG. 2. Thus, an evaporator condensate, containing the same contents of the nutrients as used in Example 1, was fed through a liquid feed pipe 6 to a first closed type trickling filter 4 provided with 15 liters of a filtering medium 10 and, then, fed via a pump 7 to a second closed type trickling filter 5 provided with 15 liters of a filtering medium 11. The treated condensate was discharged from a liquid discharge pipe 8. The discharged condensate was returned to the liquid feed pipe 6 and recirculated in the system. Into this circulation system air was blown into the system through a gas feed pipe 9 and a strain of Cephalosporium sp. FERM-P No. 3976 was inoculated. After the inoculation of the strain, pre-cultivation was carried out at a temperature of 30° C., for 7 days, to attach the strain of the fungus to the surfaces of the filtering media 10 and 11.

After the malodorous sulfur compounds contained in the circulating liquid were removed, about 150 ml/min of a non-condensible gas vaporized from a bad odor drain discharged from a kraft pulp mill was continuously fed through the gas feed pipe 9 to the vessel 10 and 11, while the liquid was circulated in the system. The treated gas was discharged from a gas discharge pipe 12. The concentrations of the malodorous sulfur compounds contained in the gas vaporized from the drain and the treated discharge gas after 6 days of operation are shown in Table 3 below.

TABLE 3

| | (ppm) | | | |
|---|---|---|---|---|
| | $H_2S$ | $CH_3SH$ | $(CH_3)_2S$ | $(CH_3)_2S_2$ |
| Gas Vaporized from Drain | 5 | 60 | 53 | 81 |
| Treated Discharge Gas (After 6 Days' Operation) | 0.1 | 0.5 | 0.5 | 2.5 |

As is clear from Table 3, the malodorous sulfur compounds were remarkably removed from the gas by the use of Cephalosporium sp. FERM-P No. 3976.

EXAMPLE 3

30 to 40 ml/min of a simulated gas in petroleum refinery plant was deodorized using the same procedure as described in Example 2, except that Aspergillus sp. FERM-P No. 3980 was used instead of Cephalosporium sp. FERM-P No. 3976. The concentrations of the malodorous sulfur compounds contained in the simulated gas and the treated discharge gas after 6 days of operation are shown in Table 4 below.

TABLE 4

|  | $H_2S$ | $CH_3SH$ | $(CH_3)_2S$ | Thiophene |
|---|---|---|---|---|
| Simulated Gas | 0.1 | 0.2 | 0.2 | 0.2 |
| Treated Discharge Gas (After 6 Days' Operation) | 0.01 | 0.01 or less | 0.01 or less | 0.1 |

As is clear from Table 4, the malodorous sulfur compounds were remarkably removed from the gas by the use of Aspergillus sp. FERM-P No. 3980.

EXAMPLE 4

Into 1 liter of an evaporator condensate derived from a kraft pump mill, 5 g of glucose, 2 g of $NH_4NO_3$, 2 g of $KH_2PO_4$, 0.5 g of $MgSO_4$ and 0.5 g of yeast extract were added. The pH of the mixture was adjusted to 6.5 and, then, the mixture was sterilized in a shake-flask. Into the flask, a strain of Cephalosporium sp. FERM-P No. 3976 was inoculated and subjected to a shake incubation, at a temperature of 30° C., for 3 days. The cultivated fungus was filtered through a filter paper and, then, washed with a distilled water. Thus, 2.0 g (dry weight) of the washed cells of the fungi were obtained.

Into a 1.2 liter conical flask, 1 liter of an evaporator condensate discharged from a kraft pulp mill was charged and, then, 2.0 g of the cells of the fungus obtained as mentioned above was added into the flask. Thereafter, the evaporator condensate and the washed cells of the fungi were contacted with each other at a temperature of 30° C. for 4 hours, while the contents of the flask were stirred by means of a magnetic stirrer. The results are shown in Table 5 below.

TABLE 5

|  | Gas Concentration in Gas Phase of Conical Flask (ppm) | | | |
|---|---|---|---|---|
|  | $H_2S$ | $CH_3SH$ | $(CH_3)_2S$ | $(CH_3)_2S_2$ |
| Before Addition of Fungi | 1.5 | 60 | 83 | 102 |
| 4 Hours After Addition of Fungi | 0.1 | 1.5 | 1.0 | 4.2 |

As is clear from Table 5, the malodorous sulfur compounds were remarkably removed from the condensate of the use of Cephalosporium sp. FERM-P No. 3976.

EXAMPLE 5

A non-condensible gas vaporized from a drain discharged from a kraft pulp mill was treated by using an apparatus as illustrated in FIG. 3. Thus, the gas was continuously fed through the gas inlet 19 to the packed column 13, while the liquid 16 having the following composition was circulated in the system.

|  | g/liter |
|---|---|
| glucose | 5 |
| peptone | 1 |
| corn steep liquor | 1 |
| Cephalosporium sp. FERM-P No. 3976 | 2 |

The residence time of the gas in the column was about 1 hr. The results are shown in Table 6.

TABLE 6

|  | (ppm) | | | |
|---|---|---|---|---|
|  | $H_2O$ | $CH_3SH$ | $(CH_3)_2S$ | $(CH_3)_2S_2$ |
| Feed Gas | 10 | 80 | 52 | 30 |
| Treated Discharge Gas | 0.1 | 0.3 | 0.2 | 1.5 |

What we claim is:

1. A method for removing odor from a fluid containing malodorous substances derived from sulfur compounds selected from the group consisting of hydrogen sulfide, methyl mercaptan, dimethyl sulfide, dimethyl disulfide and thiophene, comprising the steps of:
   (i) inoculating and cultivating at least one fungus selected from the group consisting of CEPHALOSPORIUM FERM-P No. 3976, CEPHALOSPORIUM FERM-P No. 3977, PENICILLIUM FERM-P No. 3978, PENICILLIUM FERM-P No. 3979, ASPERGILLUS FERM-P No. 3980, MUCOR FERM-P No. 3981 and TRICHODERMA FERM-P No. 3982 in a liquid medium or a solid medium in the presence of nutrients, and;
   (ii) introducing said fluid and oxygen or air into the medium containing the cultivated fungus thereby contacting said fluid with the fungus, whereby the malodorous sulfur compounds are decomposed by the action of the fungus.

2. A method for removing odor from a fluid as claimed in claim 1, wherein said fluid is an evaporator condensate discharged from a kraft pulp mill.

* * * * *